United States Patent [19]
Pugin et al.

[11] Patent Number: 6,133,464
[45] Date of Patent: Oct. 17, 2000

[54] CHIRAL FERROCENYLS

[75] Inventors: Benoît Pugin, Müchenstein; Heidi Landert, Bourrignon; Giorgio Pioda, Losone, all of Switzerland

[73] Assignee: Novartis AG, Basel, Switzerland

[21] Appl. No.: 09/254,527

[22] PCT Filed: Oct. 6, 1997

[86] PCT No.: PCT/EP97/05480

§ 371 Date: Mar. 8, 1999

§ 102(e) Date: Mar. 8, 1999

[87] PCT Pub. No.: WO98/15565

PCT Pub. Date: Apr. 16, 1998

[30] Foreign Application Priority Data

Oct. 7, 1996 [CH] Switzerland ............................ 2440/96
Oct. 7, 1996 [CH] Switzerland ............................ 2441/96

[51] Int. Cl.[7] ............................. C07F 17/02; C07F 19/00
[52] U.S. Cl. ................................. 556/14; 556/22; 556/28; 556/145; 549/313; 549/325; 560/24; 560/41
[58] Field of Search ................................ 556/14, 22, 28, 556/145; 549/313, 325; 560/24, 41

[56] References Cited

U.S. PATENT DOCUMENTS

| | | | |
|---|---|---|---|
| 5,244,857 | 9/1993 | Pugin et al. | 502/167 |
| 5,252,751 | 10/1993 | Pugin et al. | 549/214 |
| 5,371,256 | 12/1994 | Togni et al. | 556/14 |
| 5,466,844 | 11/1995 | Spindler et al. | 556/11 |
| 5,583,241 | 12/1996 | Spindler | 556/143 |
| 5,627,293 | 5/1997 | Pugin | 556/11 |
| 5,783,715 | 7/1998 | Pugin | 556/11 |
| 5,925,778 | 7/1999 | Pugin | 556/144 |
| 6,015,919 | 1/2000 | Pugin | 556/145 |

FOREIGN PATENT DOCUMENTS

| | | |
|---|---|---|
| 0496699 | 7/1992 | European Pat. Off. . |
| 0496700 | 7/1992 | European Pat. Off. . |
| 00564406 | 10/1993 | European Pat. Off. . |
| 0729969 | 9/1996 | European Pat. Off. . |
| 9632400 | 10/1996 | WIPO . |
| 9702232 | 1/1997 | WIPO . |

OTHER PUBLICATIONS

Achiwa, K., "Catalytic Asymmetric Hydrogenations with Polymer Suported Chiral Pyrrolidinephosphine–Rhodium Complexes," Chemistry Letters, 1978, pp. 905–908.
Butler et al., "The Synthesis of –N,N–dimethy–1'–diphenylphosphinoferrocenylethylamine and related ligands," Canadian Journal of Chemistry, vol. 61, 1983, pp. 147–153.
Chemical Abstract 112:36097g (1990).
Chemical Abstract 113:550c(1990).
Chemical Abstract 122:133349e (1995).
Cullen et al., "Polymer Supported Ferrocene Derivatives. Catalytic Hydrosilylatio of Olefins by Supported Palladium and Platinum Complexes," Journal of Organometalic Chemistry, vol. 333, 1987, pp. 269–280.
Hayashi T., "Asymmetric Catalysis with Chiral Ferrocenylphosphine Ligands," VCH Publishers, New York, 1995, pp. 105–142.
Kim et al., "Functionalized Organometallic Ligand (1)Synthesis of Some Ferrocene Derivatives of Cyclohexyl–and Cyclopentadienyl–phosphines," Bull. Korean Chem. Soc., vol. 13, No. 6, 1992, pp. 588–592.
Knox et al., "Ferrocene Derivatives. Part XVI. The Aminomethylation of Methyl–thio–and Bismethylthio–ferrocene," Journal of the Chemical Society (C), 1967, pp. 1842–1847.
Kovar e al., "A Convenient Route to 1'1'–Dihalogentated Ferrocenes," Organometallics in Chemical Synthesis, vol. 1, 1970/1971, pp. 173–181.
Naiini et al., "Synthesis of New Ferrocenyl Amine Sulfide and Selenide Complexes of Group 10 Metals and Their Catalytic Activities Toward Selective Hydrogenation, Isomerization, and Asymmetric Grignard Cross–coupling Reactions," Journal of Organometallic.
Pastor, S.D., "New Chiral Thio–and Seleno–Substituted Ferrocenylamines," Tetrahedron, vol. 44 (10), 1988, pp. 2883–2886.
Togni et al., "Chiral Cooperativity: The Nature of the Diastereoselective and Enantioselective Step in the Gold(I)–Catalyzed Aldol Reaction Utilizing Chiral Ferocenylamine Ligands," J. Org. Chem., vol. 55, 1990, pp. 1649–1664.
Togni, A. "Developing New Chiral Ferrocenyl Ligands for Asymmetric Catalysis: A Personal Account," Chimia, vol. 50, 1996, pp. 86–93.
Lai et al., "New Chiral Ferrocenylamine Sulfide and Selenide Ligands: Preparation, Characterization and Their Palladium and Platinum Complexes as Catalysts for Selective Hydrogenation," Inorganica Chimica Act, vol. 164, 1989, pp. 205–210.

*Primary Examiner*—Porfirio Nazario-Gonzalez
*Attorney, Agent, or Firm*—Wenderoth, Lind & Ponack, L.L.P.

[57] ABSTRACT

The invention relates to chiral ferrocenyls of formula (I)

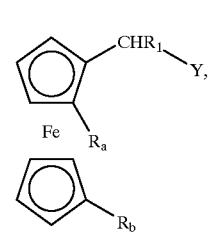

wherein $R_a$ is —P($R_{10}R_{11}$) or —S$R_{12}$;

$R_b$ is —P($R'_{10}R'_{11}$), —S$R'_{12}$, —CH=N$R_{12}$, —CH$_2$—NH—$R_{12}$ or —CH$_2$—O—P($R_{10}R_{11}$); and the other substituents are as defined in claim 1, which may be used as ligands for transition metal catalysts in enantioselective reactions.

15 Claims, No Drawings

CHIRAL FERROCENYLS

The invention relates to chiral ferrocenes substituted in the 1- and 1'-positions by two different radicals and also substituted in the 2-position, according to the general formula (I), to processes for their preparation and to the use thereof as ligands in catalysis.

Metal complexes having chiral ferrocenyl ligands are known as catalysts for a number of reactions (e.g. enantioselective hydrogenation, hydrosilylation, formation of C—C bonds). The task of the chiral ligands is firstly so to adjust the electronic environment on the metal that a catalystic cycle becomes possible and secondly to transfer the chiral information to the substrate. Hitherto there has been no model that makes it possible to predict which chiral ligand will be best (especially in respect of enantioselectivity) for the catalytic reaction of a substrate. It is therefore advantageous if the electronic and steric properties of a ligand can be coordinated within a wide range both roughly and precisely.

Most of the diphosphine ligands described hitherto, however, contain two identical phosphines. That applies also to the chiral ferrocenyl ligands described by T. Hayashi et al. which have already been used successfully in a large number of catalytic reactions. Those ligands correspond, for example, to the following formula:

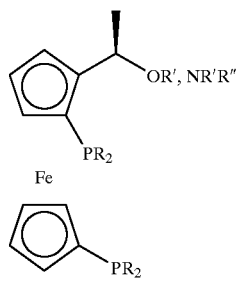

and are described in T. Hayashi, Ferrocenes (Ed.: A. Togni and T. Hayashi), VCH Publishers New York (1995) 105–142.

Examples of chiral ferrocenyl ligands having at least one sulfur radical are:

(A)

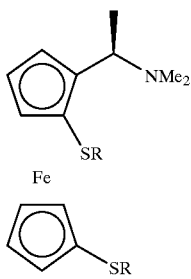

C. K. Lai, A. A. Naiini and C. H. Brubaker, Inorg. Chim. Acta, 164 (1989) 205-10.

(B)

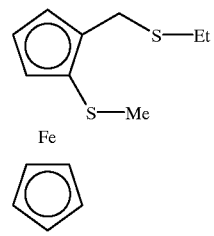

C. H. Wang and C. H. Brubaker, J. Mol. Catal., 75 (1992) 221–33.

(C)

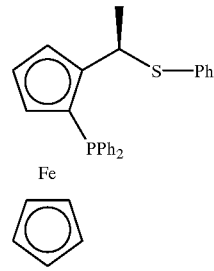

Y. Nishibayashi, K. Segawa, J. D. Singh, S. Fukuzawa, K. Ohe and S. Uemera, Organometallics, 15 (1996) 370-9.

A synthesis method is described hereinbelow that for the first time makes it possible to prepare chiral ferrocenyl ligands selectively having two different radicals in the 1,1'-position. Preferably the two different radicals are two different phosphine radicals or sulfur radicals or a sulfur radical and a phosphine radical. This makes it possible to adjust the electronic and steric properties of the chiral ferrocenyls according to the invention and of their metal complexes within a very wide range.

The invention relates to compounds of the formula (I)

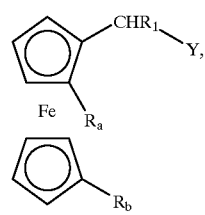

wherein $R_1$ is $C_1$–$C_8$alkyl, $C_5$–$C_{12}$cycloalkyl, phenyl or phenyl substituted by from 1 to 3 substituents selected from $C_1$–$C_4$alkyl and $C_1$–$C_4$alkoxy;

$R_a$ is —P($R_{10}R_{11}$) or —S$R_{12}$;

$R_b$ is —P($R'_{10}R'_{11}$), —S$R'_{12}$, —CH=N$R_{12}$, —CH$_2$—NH—$R_{12}$ or —CH$_2$—O—P($R_{10}R_{11}$);

$R_{10}$ and $R_{11}$ are each independently of the other $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —Si$R_4R_5R_6$, halogen, —SO$_3$M, —CO$_2$M, —PO$_3$M, —NR$_7$R$_8$, —[$^+$NR$_7$R$_8$R$_9$]X$^-$ and $C_1$–$C_5$fluoroalkyl; or $R_{10}$ and $R_{11}$ together are $C_4$–$C_8$alkylene, $C_4$–$C_8$alkylene substituted by $C_1$–$C_4$alkyl or by phenyl, or annelated $C_4$–$C_8$alkylene;

$R'_{10}$ and $R'_{11}$ are each independently of the other as defined by $R_{10}$ and $R_{11}$, with the proviso that —$P(R_{10}R_{11})$ is not identical to —$P(R'_{10}R'_{11})$;

$R_{12}$ is H, $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —$[^+NR_7R_8R_9]X^-$ and $C_1$–$C_5$fluoroalkyl;

$R'_{12}$ is as defined by $R_{12}$, with the proviso that —$SR_{12}$ is not identical to —$SR'_{12}$;

$R_4$, $R_5$ and $R_6$ are each independently of the others $C_1$–$C_{12}$alkyl or phenyl;

$R_7$ and $R_8$ are each independently of the other H, $C_1$–$C_{12}$alkyl or phenyl, or $R_7$ and $R_8$ together are tetramethylene, pentamethylene or 3-oxa-1,5-pentylene, $R_9$ is H or $C_1$–$C_4$alkyl;

M is H or an alkali metal;

$X^-$ is the anion of an acid;

Y is —$OR_{13}$, —$SR_{14}$ or —$NR_{15}R_{16}$;

$R_{13}$ is H, $C_1$–$C_{18}$alkyl, —C(O)—$C_{1-8}$alkyl, phenyl or phenyl substituted by from one to three substituents selected from $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —$[^+NR_7R_8R_9]X^-$ and $C_1$–$C_5$fluoroalkyl;

$R_{14}$ is H, $C_1$–$C_{18}$alkyl, phenyl or phenyl substituted by from one to three substituents selected from $C_1$–$C_4$alkyl, $C_1$–$C_4$-alkoxy, —$SiR_4R_5R_6$, halogen, —$SO_3M$, —$CO_2M$, —$PO_3M$, —$NR_7R_8$, —$[^+NR_7R_8R_9]X^-$ and $C_1$–$C_5$-fluoroalkyl; and $R_{15}$ and $R_{16}$ are each independently of the other $C_1$–$C_{18}$alkyl that may be substituted and/or interrupted by one or more hetero atoms, arylenes or carbocycles; or —$NR_{15}R_{16}$ is a cyclic amine with the proviso that $R_a$ is not —$CH_3$ and Y is not —$N(H_3)_2$, when $R_a$ is —$P(C_6H_5)$, and $R_b$ is —$P[C(CH_3)_3]_2$ or when $R_a$ is —$P[C(CH_3)_3]_2$ and $R_b$ is —$P(C_6H_5)_2$.

Preferred compounds of formula (I) are those in which $R_a$ is —$P(R_{10}R_{11})$ and $R_b$ is —$P(R'_{10}R'_{11})$, at least one substituent $R_{10}$, $R'_{10}$, $R_{11}$ or $R'_{11}$ having a chemical structure that is different from the other substituents; especially preferably $R_{10}$ and $R'_{10}$ and also $R_{11}$ and $R'_{11}$ have a different chemical structure for one another.

Examples of $R_1$ as alkyl are methyl, ethyl, n-propyl and isopropyl, n-butyl, osibutyl and tert-butyl, pentyl, hexyl, heptyl and octyl, Linear alkyl is preferred. It contains preferably from 1 to 4 carbon atoms. Methyl and ethyl are preferred, with methyl being especially preferred.

$R_1$ as cycloalkyl preferably contains from 5 to 8, especially 5 or 6, ring carbon atoms. Examples of cycloalkyl are cyclopentyl, cyclohexyl, cycloheptyl, cyclooctyl, cyclodecyl and cyclododecyl. Cyclopentyl and cyclohexyl are preferred, with cyclohexyl being especially preferred.

$R_1$ contains as substituted phenyl preferably 1 or 2 substituents. Alkyl substituents may be, for example, methyl, ethyl, n-propyl and isopropyl, n-butyl, isobutyl and tert-butyl, with methyl and ethyl being preferred. Alkoxy substituents may be, for example, methoxy, ethoxy, n-propoxy and isopropoxy, n-butyoxy, isobutoxy and tert-butoxy, with methoxy and ethoxy being preferred. In a group of compounds of formula I, $R_1$ is preferably phenyl or phenyl substituted by 1 or 2 $C_1$–$C_4$alkyl or $C_1$–$C_4$alkoxy substituents.

$R_{10}$, $R_{11}$ and $R_{12}$, and $R'_{10}$, $R'_{11}$ and $R'_{12}$, as alkyl may be linear or branched and contain preferably from 1 to 8, especially from 1 to 4, carbon atoms. Examples of that alkyl are methyl, ethyl, n-propyl and isopropyl, n-butyl, isobutyl and tert-butyl, pentyl, hexyl, heptyl, octyl, nonyl, decyl, undecyl and dodecyl. Methyl, ethyl, n-propyl and isopropyl, n-butyl, isobutyl and tert-butyl are preferred. When $R_{10}$ and $R_{11}$, and $R'_{10}$ and $R'_{11}$, are identical, as alkyl they are especially isopropyl or tert-butyl.

$R_{10}$, $R_{11}$ and $R_{12}$, and $R'_{10}$, $R'_{11}$ and $R'_{12}$, as substituted alkyl are derived from the above-mentioned alkyl, with alkyl having from 1 to 3 carbon atoms being especially preferred. Phenyl is preferred as substituent. Examples of that alkyl are benzyl, 1- and 2-ethylphenyl and n-propylphenyl and iso-propylphenyl.

$R_{10}$, $R_{11}$ and $R_{12}$, and $R'_{10}$, $R'_{11}$ and $R'_{12}$, as cycloalkyl preferably contain from 5 to 8, especially 5 or 6, ring carbon atoms. Examples of cycloalkyl are cyclopentyl, cyclohexyl, cycloheptyl, cyclooctyl, cyclodecyl and cyclododecyl. Cyclopentyl and cyclohexyl are preferred, with cyclohexyl being especially preferred.

The cycloalkyl may be substituted, for example by from 1 to 3 alkyl or alkoxy substituents. Examples of such substituents have been given above. Methyl and ethyl and methoxy and ethoxy are preferred. Examples of substituted cycloalkyl are methyl- and methoxy-cyclopentyl and -cyclohexyl.

$R_{10}$, $R_{11}$ and $R_{12}$, and $R'_{10}$, $R'_{11}$ and $R'_{12}$, as substituted phenyl preferably contain 1 or 2 substituents. When the phenyl contains 2 or 3 substituents, those substituents may be identical or different.

Examples of the substituents alkyl and alkoxy have been given above; preferred alkyl and alkoxy substituents for phenyl are methyl, ethyl and also methoxy and ethoxy.

When the phenyl substituent is halogen, it is preferably —F, —Cl or —Br.

When the phenyl substituent is $C_1$–$C_5$ fluoroalkyl, it is wholly or partially fluorinated $C_1$–$C_5$alkyl. Examples thereof are the position isomers of mono- to deca-fluoropentyl, mono- to octa-fluorobutyl, mono- to hexa-fluoropropyl, mono- to tetra-fluoroethyl and mono- and di-fluoromethyl. Of the partially fluorinated alkyl radicals, those of the formulae —$CF_2H$ and —$CF_2(C_1$–$C_4$alkyl) are especially preferred. A perfluorinated alkyl is especially preferred. Examples thereof are perfluoropentyl, perfluorobutyl, perfluoropropyl, perfluoroethyl and especially trifluoromethyl. The fluoro-substituted alkyl groups are preferably bonded in the 3-, 4- and 5-positions.

When $R_{10}$ and $R_{11}$ together are $C_4$–$C_8$alkylene, $C_4$–$C_8$alkylene substituted by $C_1$–$C_4$alkyl or by phenyl, or annelated $C_4$–$C_8$alkylene, they are preferably a radical of formula IV, IVa, IVb or IVc

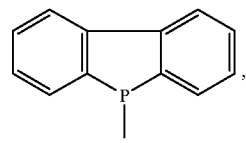

(IV)

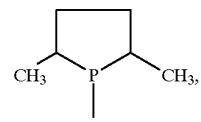

(IVa)

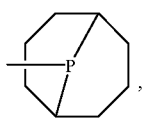

(IVb)

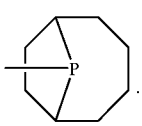

(IVc)

$R_4$, $R_5$ and $R_6$ may be linear or branched alkyl that preferably contains from 1 to 8, especially from 1 to 4, carbon atoms. Examples of alkyl have been given above. Preferred alkyl is methyl, ethyl, n-propyl, n-butyl and tert-butyl. Especially preferably the substituent —$SiR_4R_5R_6$ is trimethylsilyl.

Of the acidic phenyl substituents —$SO_3M$, —$CO_2M$ and —$PO_3M$, the groups —$SO_3M$ and —$CO_2M$ are preferred. M is preferably H, Li, Na or K.

$R_7$ and $R_8$ contain as alkyl preferably from 1 to 6, especially from 1 to 4, carbon atoms. The alkyl is preferably linear. Preferred examples are methyl, ethyl, n-propyl and n-butyl. $R_9$ as alkyl is preferably methyl.

$X^-$ as an anion of an acid is preferably $Cl^-$, $Br^-$ or the anion of a carboxylic acid, for example formate, acetate, trichloroacetate or trifluoroacetate, or $BF_4^-$, $PF_6^-$ or $SO_4^{2-}$.

Preferred examples of $R_{10}$, $R_{11}$ and $R_{12}$, and $R'_{10}$, $R'_{11}$ and $R'_{12}$, as substituted phenyl are 2-methyl-, 3-methyl-, 4-methyl-, 2- or 4-ethyl-, 2- or 4-isopropyl-, 2- or 4-tert-butyl-, 2-methoxy-, 3-methoxy-, 4-methoxy-, 2- or 4-ethoxy-, 4-trimethylsilyl-, 2- or 4-fluoro-, 2,4-difluoro, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$-, 2- or 4-$SO_3Na$-, 2- or 4-[$^+NH_3Cl^-$]-, 3,4,5-trimethyl-,2,4,6-trimethyl-, 4-trifluoromethyl- and 3,5-di-(trifluoromethyl)-phen-1-yl.

Especially preferably $R_{10}$, $R_{11}$ and $R_{12}$, and $R'_{10}$, $R'_{11}$ and $R'_{12}$, are cyclohexyl, n-butyl, sec-butyl, tert-butyl, phenyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl and 3,5-dimethyl-4-methoxyphen-1-yl, with cyclohexyl, phenyl, 4-methylphen-1-yl and n- and tert-butyl being especially preferred.

$R_{13}$ and $R_{14}$ may be as defined hereinbefore by way of example for alkyl and substituted phenyl. Preferably $R_{13}$ and $R_{14}$ are H, $C_1$–$C_4$alkyl or phenyl.

$R_{15}$ and $R_{16}$ may be linear or branched $C_1$–$C_{18}$alkyl analogously to the definitions given hereinbefore by way of example.

$R_{15}$ and $R_{16}$ as substituted alkyl may be $C_1$–$C_{18}$alkyl substituted by halogen, —OH, $C_1$–$C_8$alkoxy, aryloxy (such as phenyloxy or substituted phenyloxy), —SO, $C_1$–$C_8$alkylthio, arylthio (such as thiophenyl), —$NH_2$, primary or secondary $C_1$–$C_8$amine or by aryl (such as phenyl or naphthyl).

$R_{15}$ and $R_{16}$ as alkyl interrupted by one or more hetero atoms, arylenes or carbocycles may be alkyl comprising groups such as —($CH_2CH_2O$)—, —($CH_2CH_2CH_2O$)—, —($CH_2CH_2S$)—, —($CH_2CH_2CH_2S$)—, —($CH_2CH_2NH$)—, —($CH_2NHCH_2$)—, —($CH_2N(C_1$–$C_8$alkyl)$CH_2$)—, —($CH_2(C_6H_4)$)— or —($CH_2(C_6H_{10})$)—.

$R_{15}$ and $R_{16}$ as cyclic amine may be unsubstituted or substituted cyclic amines having a ring size of from 4 to 10, especially 5 or 6, atoms. Substituents are, for example, $C_1$–$C_8$alkyl or $C_1$–$C_8$alkylamine. In addition to the amine function, the ring may contain further hetero atoms, for example —O—, —S—, —NH— or —Nalkyl—.

Preferably Y is the group —$NR_{15}R_{16}$. Especially preferably —$NR_{15}R_{16}$ is —$N(CH_3)_2$, —$N(C_3H_5)_2$, —$N(n$-$C_3H_7)_2$, —$N(iso$-$C_3H_7)_2$, —$N(n$-$C_4H_9)_2$, pyrrolidyl, piperidyl, —$N(CH_3)CH_2C_3F_7$, —$N(CH_3)C_2H_4OH$, —$N(CH_3)C_2H_4OCH_3$, —$N(CH_3)CH(CH_2OH)_2$, —$N(CH_3)CH(CH_2OH)_2$, —$N(CH_3)C_2H_4N(CH_3)_2$, —$N(CH_3)C_2H_4N(CH_3)H$, —$N(CH_3)C_2H_4N(C_2H_5)_2$, —$N(C_2H_4OH)_2$, —$N(CH_3)C_2H_4N(C_5H_{10})$, —$N(CH_3)C_2H_4N(C_2H_4OC_2H_4)$ or —$N(CH_3)C_2H_4N(C_2H_4OC_2H_4OC_2H_4N(CH_3)C_2H_4OC_2H_4OC_2H_4)$.

Compounds of the formulae

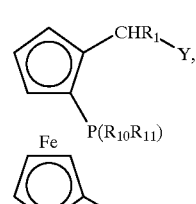

(Ia)

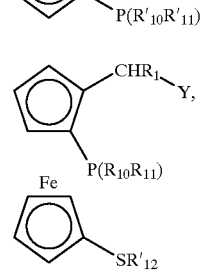

(Ib)

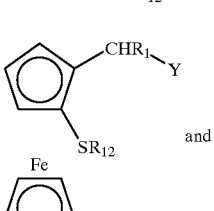

(Ic)

and

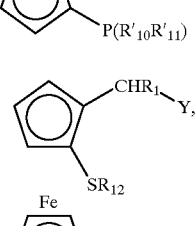

(Id)

wherein the substituents have the above-mentioned definitions and preferred meaning, are especially preferred.

The compounds of formula (I) according to the invention can be obtained in accordance with the following process.

Starting from a compound of formula (II)

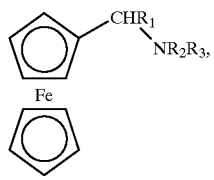

(II)

wherein $R_1$ is $C_1$–$C_8$alkyl, $C_5$–$C_{12}$cycloalkyl, phenyl or phenyl substituted by from 1 to 3 substituents selected from $C_1$–$C_4$alkyl and $C_1$–$C_4$alkoxy;

$R_2$ and $R_3$ are each independently of the other hydrogen or $C_1$–$C_{12}$alkyl;

that compound is reacted in an inert organic solvent first with one equivalent of alkyl-lithium and then, in the presence of an amine complexing agent for Li, with a second equivalent of alkyl-lithium, and the product is then reacted with a halogenating agent to form compounds of formula (III)

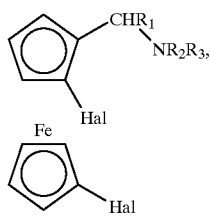

(III)

wherein Hal is F, Cl, Br or I.

$R_2$ and $R_3$ as alkyl may be linear or branched. Examples of $C_1$- to $C_8$-alkyl have been given above; additionally there may be mentioned the various isomers of nonyl, decyl, undecyl and dodecyl, $R_2$ and $R_3$ may also be bonded to one another and may form a cyclic alkyl group. Examples are pyrrolidine or piperidine.

Preferably $R_2$ and $R_3$ are each independently of the other methyl or ethyl; especially preferably they are both methyl.

An example of an amine complexing agent for Li is N,N,N,N-tetramethylethylenediamine.

Within the context of this invention, alkyl-lithium is to be understood as being preferably tert-butyl-, sec-butyl- or n-butyl-lithium.

Halogenating agents are known in the general prior art for many reactions. For example, a number are mentioned in Gmelin, Handbuch der Anorganischen Chemie (Handbook of Inorganic Chemistry), Ferroorganic Compounds Part A Ferrocene 7, Eighth Edition, Springer Verlag 1908, pages 128–136.

Preferably the halogenating agent is selected from the group consisting of $Cl_2$, hexachloroethane, 1,2-dichlorotetrafluoroethane, toluene-4-sulfonyl chloride, $Br_2$, 1,2-dibromotetrachloroethane, 1,2-dibromotetrafluoroethane, toluene-4-sulfonyl bromide, 2,3-dimethyl- 2,3-dibromobutane, $I_2$, 1,2-diiodotetrafluoroethane, perfluoropropyl iodide, perfluoroethyl iodide, toluene-4-sulfonyl iodide and perfluoromethyl iodide.

In a first step alkyl-lithium is added to the compounds of formula (III) in an inert organic solvent and allowed to react and then in a second step an organic solution of a compound of formula $ClP(R_{10}R_{11})$ (Va) or of formula $R_{12}SSR_{12}$ (Vb) is added, yielding compounds of formula

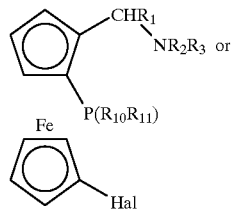

(VIa)

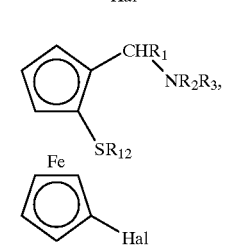

(VIb)

wherein $R_{10}$, $R_{11}$ and $R_{12}$ have the definitions and preferred meaning given above.

The substitution by the halogen atom takes place predominantly on the cyclopentadienyl ring that carries the second substituent (alkylamine).

The process is preferably carried out by adding alkyl-lithium at a temperature of from −90 to +30° C.

In the second step, the compounds of formula (Va) or (Vb) are preferably added at a temperature of from −90 to +30° C.

The compounds of formula (VIb) are novel and constitute a further aspect of this invention.

The compounds of formula (Ia) are obtainable by adding alkyl-lithium to compounds of formula (VIa), in an inert organic solvent, analogously to the above preparation process for the preparation of compounds of formula (VIa), causing the mixture to react and subsequently in a second step adding an organic solution of a compound of formula $ClP(R'_{10}R'_{11})$ (Vd), wherein $R'_{10}$ and $R'_{11}$ have the definitions and preferred meaning given above, and optionally converting the radical —$NR_2R_3$ into the radical —Y.

The compounds of formula (Ib) are obtainable by adding alkyl-lithium to compounds of formula (VIa), in an inert organic solvent, analogously to the above preparation process for the preparation of compounds of formula (VIb), causing the mixture to react and subsequently reacting it with an organic solution of a compound of formula $R'_{12}SSR'_{12}$ (Vc), wherein $R'_{12}$ has the definitions and preferred meaning given above, and optionally converting the radical —$NR_2R_3$ into the radical —Y.

Compounds having $SR_{12}$ or $SR'_{12}$ wherein $R_{12}$ or $R'_{12}$ is hydrogen can be prepared analogously to "Ferrocenes, Editors A. Togni and T. Hayashi, VCH Publishers 1995", pages 231–233.

The compounds of formulae (Ic) and (Id) are obtainable by adding alkyl-lithium to compounds of formula (VIb), in an inert organic solvent, analogously to the above preparation process for the preparation of compounds of formula (VIa) or (VIb), causing the mixture to react and subsequently reacting it with an organic solution of a compound of formula $ClP(R'_{10}R'_{11})$ (Vd) or of formula $R'_{12}SSR'_{12}$ (Vc), wherein $R_{10}$, $R_{11}$ and $R'_{12}$ have the definitions and preferred meaning given above, and optionally converting the radical —$NR_2R_3$ into the radical —Y.

The preparation of the compounds of formulae (I) and especially (Ia), (Ib), (Ic) and (Id) constitutes a further aspect of this invention.

The compounds of formula (I), (VIa) or (VIb) may be obtained in the form of racemates, pure enantiomers or mixtures of enantiomers. If the synthesis is carried out using enantiomerically pure compounds of formula (II) as starting materials, there are formed very preferentially only one of the two possible diastereoisomers of the compounds of formula (III) and consequently also of the compounds of formulae (VIa) and (VIb) and (I).

If racemates or optically active mixtures are used as starting materials, they can be separated into the stereoisomers by means of known methods, with chromatographic methods or crystallisation generally being preferred.

Isolation and purification of the compounds is carried out in accordance with methods known per se, for example distillation, extraction, crystallisation and/or chromatographic methods.

The compounds of formula (I) wherein $R_b$ is —CH=NR$_{12}$ or —CH$_2$—NH—R$_{12}$ can be prepared starting from a compound of formula (VIa) or (VIb) by converting the halogen radical into a radical —CHO and subsequently reacting the product with a primary amine. The radical —CH=NR$_{12}$ can be converted into the radical —CH$_2$—NH—R$_{12}$ by further reaction with a reducing agent, such as LiAlH$_4$. The general reaction conditions are known to the person skilled in the art and may be generalized from the following Examples.

The compounds of formula (I) wherein $R_b$ is —CH$_2$—O—P(R$_{10}$R$_{11}$) can be prepared starting from a compound of formula (VIa) or (VIb) by converting the halogen radical into a radical —CHO and subsequent reduction with a reducing agent, such as LiAlH$_4$, to form the alcohol, which is reacted with a chlorophosphine of formula ClP(R$_{10}$R$_{11}$). The general reaction conditions are known to the person skilled in the art and may be generalized from the following Examples.

To prepare further compounds of formulae (I) and especially (Ia), (Ib), (Ic) and (Id), the group NR$_2$R$_3$ can be converted into the various groups defined for Y in accordance with the following scheme.

Other alternative or subsequent process steps are known to the person skilled in the art.

A further aspect of this invention is constituted by transition metal complexes with ferrocenyl ligands of formula (I) and especially (Ia), (Ib), (Ic) or (Id). $d^8$-Transition metals, such as Rh, Ir, Ru, Pd, Ni and Au, are preferred, with Rh, Pd, Ni and Ir being especially preferred.

The transition metal complexes according to the invention can be used as catalysts, for example in hydrogenations, transfer hydrogenations and hydrosilylations of double bonds (C—C, C—O or C—N), allylic substitutions, hydroformylations or cross-coupling reactions. The individual, preferably enantioselective, catalystic reactions are known from the literature, for example, also with diphosphine ligands, and the catalysts according to the invention make it possible to vary the catalyst properties in a hitherto unknown manner by means of the two different ferrocenyl radicals. The widely differentiated electronic and steric environments that are thus possible on the transition metal make it possible to increase the stereo-selectivity, activity and/or productivity. A further aspect of this invention is accordingly the use of transition metal complexes containing a compound of formula (I), and especially (Ia), (Ib), (Ic) or (Id), in enantioselective catalysis, The processes for the preparation of the transition metal complexes are analogous to those described in the literature and known to the person skilled in the art. The transition metal complexes are frequently prepared in situ, that is to say in the reaction medium in question. For example, in that process a ligand substitution by the ferrocenyls according to the invention is effected on the transition metal.

The definitions and preferred meanings for the individual substituents of the compounds of formula (I) and especially of formulae (Ia), (Ib), (Ic) and (Id) apply analogously also to the transition metal catalysts, to their preparation and to their use.

The following Examples illustrate the invention.

General process procedure

All operations are carried out under an inert gas atmosphere (argon). Ether and THF are freshly distilled over

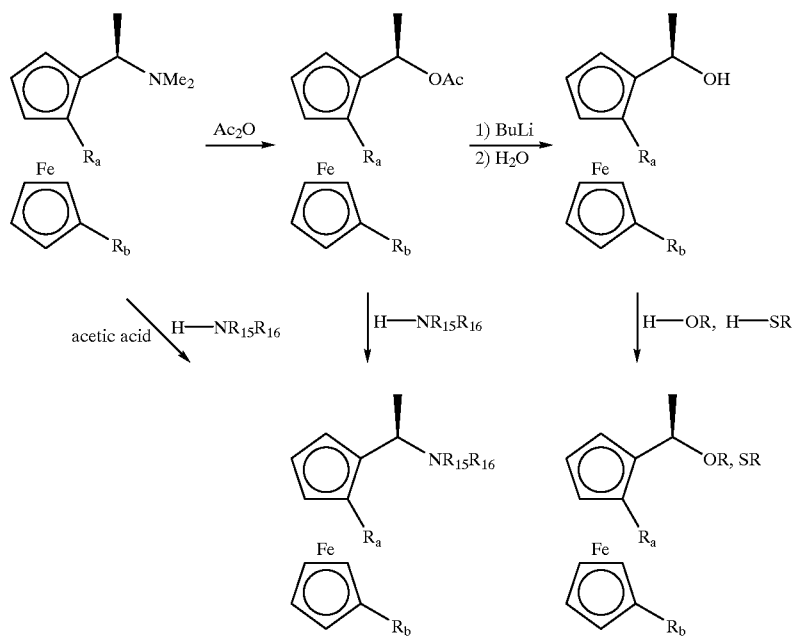

sodium/benzophenone. Hexane and pentane are dried over a Pb/Na alloy. Unless specified to the contrary, Merck 60 silica gel is used as solid phase for the purification by chromatography.

Abbreviations used
TMEDA: N,N,N,N-tetramethylethylenediamine
n-BuLi or BuLi: n-butyllithium (1.6 molar solution in hexane)
COD: 1,5-cyclooctadiene
Cyh: cyclohexyl
o-Tol: o-tolyl
Tol: toluene
NBD: norbornadiene
Hex: hexane
Ph: phenyl
Me: methyl
Cyp: cyclopentyl
Cp: cyclopentadienyl
t-Bu: tert-butyl
Ac: acetyl Example A2
Preparation of the compound of formula 2
(R)-N,N-Dimethyl-1-[(S)-1', 2bis(bromo)-ferrocenyl]ethylamine

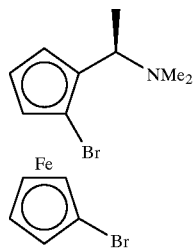

(2)

20.6 ml (33 mmol) of a 1.6M n-BuLi solution are added dropwise at room temperature, with stirring, to a solution of 7.71 g (30 mmol) of (R)-N,N-dimethyl-1-ferrocenylethylamine in 50 ml of diethyl ether. After 1.5 hours a further solution consisting of 22.5 ml (36 mmol) of a 1.6M BuLi solution in hexane and 4.95 ml (33 mmol) of TMEDA is added dropwise and the reaction mixture is stirred overnight. The dark-brown, cloudy reaction mixture is then cooled to from −72 to −78° C. using a dry ice/isopropanol bath and, with stirring, 7.9 ml (66 mmol) of 1,2-dibromotetrafluoroethane are slowly added dropwise in such a manner that the temperature of the mixture does not exceed −74° C. The mixture is stirred for a further 1 hour with cooling and then for a further 2 hours without cooling. 50 ml of ice-water are added to the resulting orange suspension and extraction is carried out by shaking with 25 ml of ethyl acetate several times. The organic phases are collected, washed with water, dried with $Na_2SO_4$ and concentrated using a rotary evaporator. The brown crude product is purified by chromatography (silica gel: Merck 60; eluant: acetone). 7.5 g of compound 2 are obtained (yield 60%, brown oil).

Analysis
$^1$H-NMR ($CDCl_3$): δ 1.53 (d, 3H, J=7, C—$CH_3$), 2.13 (s, 6H, N($CH_3$)$_2$), 3.78 (q, 1H, J=7, CH—Me), 4.03–4.5 (m, 7H, $C_5H_3FeC_5H_4$). Microanalysis calculated for $C_{14}H_{17}NBr_2Fe$: C, 40.52; H, 4.13; N, 3.38; Br, 38.51; Fe, 13.46. Found: C, 40.80; H, 4.10; N, 3.30; Br, 38.18.

Examples A4–A8

The method is described using the example of compound (4). All the other compounds are prepared analogously. Different conditions and the results are given in Table 1.

Example A4
Preparation of the compound of formula 4
(R)-N,N-Dimethyl-1-[1'-(bromo), (S)-2-(diphenylphosphino) ferrocenyl]ethylamine

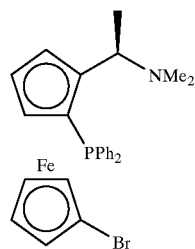

(4)

12.2 ml of a 1.6M BuLi solution in hexane (1 mmol of BuLi per mmol of starting material) are added dropwise at −30° C., with stirring, to a solution of 7.98 g (19.2 mmol) of compound (2) in 96 ml of diethyl ether (5 ml per mmol of starting material). The mixture is then cooled to from −78 to −70° C. and 4.23 ml of Cl—$PPh_2$ (1.2 mmol of chlorophosphine per mmol of starting material) are slowly added. The mixture is then allowed to warm to room temperature and is stirred for a further 2 hours. Water is then added to the resulting yellow suspension and extraction is carried out by shaking with hexane several times. The organic phases are collected, washed with water, dried with $Na_2SO_4$ and concentrated by rotary evaporation. The yellow-brown crude product is purified by chromatography (first, crude purification with silica gel: Merck 60; eluant: ethyl acetate, then chromatography over Alox; eluant tolune/hexane 1:10). 5.27 g of product are obtained (yield 53%, orange-brown, almost solid). The selectivity and yield of the reaction can be increased further if a nonpolar solvent is used. In pentane, instead of diethyl ether, a yield of more than 60% is obtained.

Analysis
$^1$H-NMR ($CDCl_3$): δ 1.25 (d, 3H, J=7, C—$CH_3$), 1.75 (s, 6H, N($CH_3$)$_2$), 4.15 (m, 1H, J=7, CH—Me), 3.7–4.4 (m, 7H, $C_5H_3FeC_5H_4$), 7.1–7.65 (m, 10H, P($C_6H_5$)$_2$) $^{31}$P-NMR ($CDCl_3$): δ −24.6

The optical purity can be verified by means of $^1$H-NMR by the formation of a complex of (4) with di-μ-chloro-[(R)-dimethyl(α-methylbenzyl)aminato-C2-N]dipalladium(II) (J. Chem. Soc., Dalton Trans., (1979) 2019): no trace of the other enantiomer is observed.

TABLE 1

| Comp. No. | R' | Amount mmol of starting mat. | Chromatogr. solid phase | Purification Eluant | Yield % | $^{31}P$ δ | $^{1}H$ δ $NMe_2$ |
|---|---|---|---|---|---|---|---|
| 4 | Ph | 19.2 | 1) Merck 60 2) Alox | ethyl acetate Tol 1/Hex 10 | 60 | −24.6 | 1.75 |
| 5 | Cyh | 7.2 | Merck 60 | ethyl acetate | 53 | −11.8 | 2.1 |
| 6 | Ph-p-$CF_3$ | 2.4 | Alox | Hex | 41 | −24.1 | 1.74 |
| 7 | Cyp | 3.9 | Merck 60 | ethyl acetate 3/Hex 1 | 45 | −20.2 | 2.1 |
| 8 | o-Tol | 7 | Merck 60 | ethyl acetate | 58 | −47.7 | 1.81 |

Diethyl ether is used as solvent except in the case of compound 4, when hexane is used.

EXAMPLES 1–11

The method is described using the example of compound (100). All the other compounds are prepared analogously. Different conditions and the results are given in table form (see Table 2):

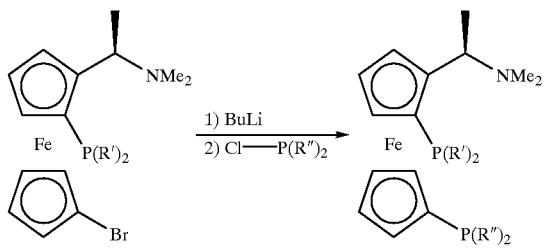

Example 1
Preparation of (R)-N,N-dimethyl-1-[1'-(dicyclohexylphosphino), (S)-2-(diphenylphosphino) ferrocenyl]ethylamine

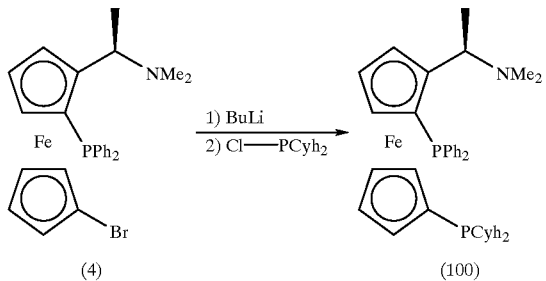

2.16 ml of a 1.6M BuLi solution in hexane (1.2 mmol of BuLi per mmol of starting material) are added dropwise at −30° C., with stirring, to a solution of 1.5 g (2.88 mmol) of (4) in 20 ml of diethyl ether (7 ml per mmol of starting material). The mixture is then cooled to from −78 to −70° C. and 0.84 g of chloro-dicyclohexylphosphine (1.25 mmol of chloro-phosphine per mmol of starting material) is slowly added. The mixture is then allowed to warm to room temperature and is stirred for a further 2 hours. Water is then added to the resulting yellow suspension and extraction is carried out by shaking with ethyl acetate several times. The organic phases are collected, washed with water, dried with $Na_2SO_4$ and concentrated by rotary evaporation. The yellow-brown crude product is purified by chromatography (silica gel: Merck 60; eluant: ethyl acetate/hexane 1/3). 1.33 g of product are obtained (yield 72.5%, orange powder).

$^{31}P$-NMR ($CDCl_3$): δ −8.1 ($PCyh_2$), −23.4 ($PPh_2$)

Table 2: Synthesis of the diphosphine compounds:

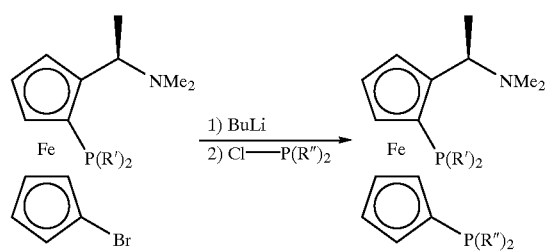

| Comp. No. | R' | R" | Starting mat. Ex. No. | Amount mmol of starting mat. | Purification Eluant | Yield % | $^{31}P$ δ $PR'_2$ | $^{31}P$ δ $PR"_2$ |
|---|---|---|---|---|---|---|---|---|
| 100 | Ph | Cyh | A4 | 2.9 | ethyl acetate 1/Hex 3 | 73 | −23.4 | −8.1 |
| 101 | Ph | Cyp | A4 | 1.76 | ethyl acetate 1/Hex 3 | 57 | −23.2 | −11.3 |
| 102 | Ph | o-Tol | A4 | 2.9 | ethyl acetate 1/Tol 2 | 30 | −23.6 | −37.6 |
| 103 | Ph | Ph-p-$CF_3$ | A4 | 0.58 | ethyl acetate 1/Hex 1 | 30 | −24.1 | −17.1 |

-continued

| Comp. No. | R' | R" | Starting mat. Ex. No. | Amount mmol of starting mat. | Purification Eluant | Yield % | $^{31}P$ δ PR'$_2$ | $^{31}P$ δ PR"$_2$ |
|---|---|---|---|---|---|---|---|---|
| 104 | Cyh | Ph | A5 | 0.3 | ethyl acetate 1/Hex 8 | 54 | −11.4 | −18.0 |
| 105 | Ph-p-CF$_3$ | Cyh | A6 | 0.29 | Hex | 47 | −22.7 | −8.5 |
| 106 | Ph-p-CF$_3$ | Ph | A6 | 0.46 | ethyl acetate 1/Tol 10 | 40 | −23.0 | −18.0 |
| 107 | Ph-p-CF$_3$ | t-Bu | A6 | 0.46 | ethyl acetate 1/Hex 2 | 62 | −22.9 | +26.8 |
| 108 | Cyp | Ph | A7 | 0.71 | ethyl acetate 1/Me Cl 1 | 84 | −20.4 | −17.6 |
| 109 | o-Tol | Cyh | A8 | 2.1 | ethyl acetate, 0.5% NEt$_3$ | 82 | −45.0 | −6.2 |
| 110 | o-Tol | Ph | A8 | 2.0 | ethyl acetate, 0.5% NEt$_3$ | 73 | −45.4 | −16.1 |

Merck 60 silica gel is used as the solid phase except in the case of compound 105, when Alox is used.

EXAMPLE 12

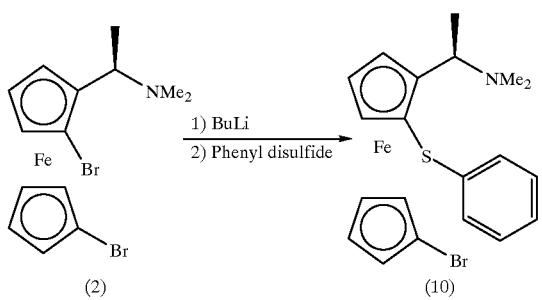

4.97 ml (7.95 mmol) of BuLi are added dropwise at approximately −40° C. over a period of 30 minutes to a solution of 3 g (7.23 mmol) of compound (2) in 42 ml of pentane, and the mixture is stirred at that temperature for a further 30 minutes. The mixture is then cooled to −78° C. and 2.05 g (9.4 mmol) of phenyl disulfide are added, cooling is removed and the mixture is stirred overnight. Saturated sodium hydrogen carbonate solution is then added to the reaction mixture and extraction is carried out 3 times with ethyl acetate. The combined organic phases are washed with saturated NaCl solution, dried over sodium sulfate, concentrated by rotary evaporation and purified by chromatography (first, silica gel: Merck 60; eluant: acetone, then Alox III; eluant: hexane/0.5% triethylamine). 1.41 g of product (100) are obtained (yield 44%, yellow powder).

EXAMPLE 13

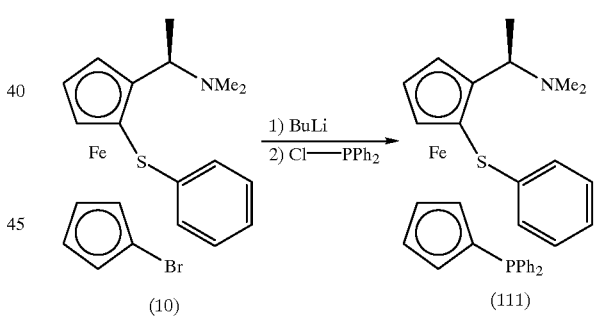

0.93 ml (1.49 mmol) of BuLi is added dropwise at approximately −40° C. to a solution of 600 mg (1.35 mmol) of compound (10) in 5 ml of diethyl ether, and the mixture is stirred at that temperature for a further 30 minutes. The mixture is then cooled to −78° C. and 0.33 ml (1.76 mmol) of chloro-diphenylphosphine is added, cooling is removed and the mixture is stirred overnight. Water is then added to the reaction mixture and extraction is carried out 3 times with ethyl acetate. The combined organic phases are washed with saturated NaCl solution, dried over sodium sulfate, concentrated by rotary evaporation and purified by chromatography (silica gel: Merck 60; eluant: acetone). 0.72 g of product is obtained (yield 97%, orange oil).

EXAMPLE 14

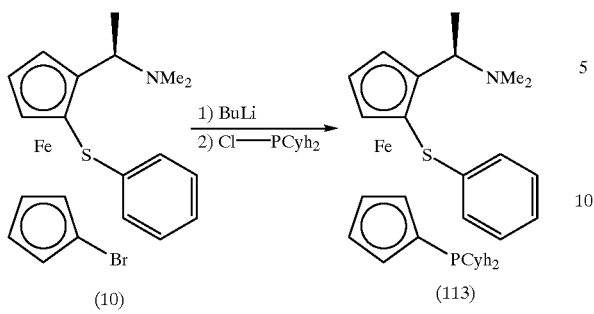

Starting with 600 mg of compound (10), compound (113) is prepared in nalogy to compound (111). 0.63 g of product is obtained (yield 83%, orange oil).

EXAMPLE 15

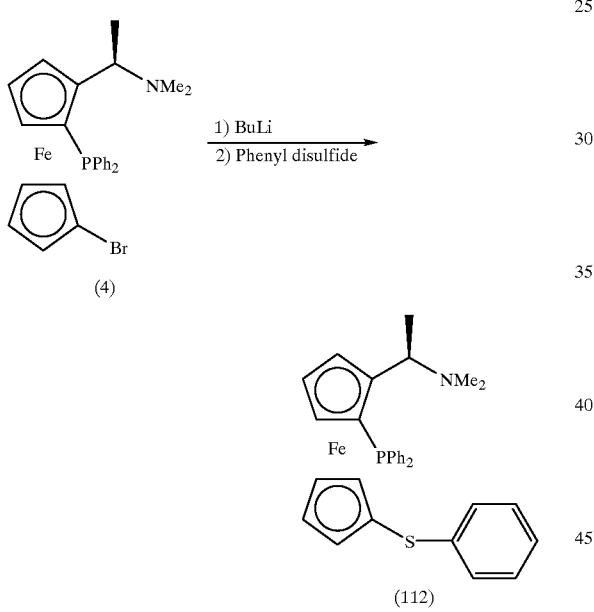

0.83 ml (1.3 mmol) of BuLi is added dropwise at −40° C. over a period of 30 minutes to a solution of 626 mg (1.2 mmol) of compound (4) in 10 ml of diethyl ether, and the mixture is stirred at that temperature for a further 30 minutes. The mixture is then cooled to −78° C. and 341 mg (1.56 mmol) of phenyl disulfide are added, cooling is removed and the mixture is stirred overnight. Saturated sodium hydrogen carbonate solution is then added to the reaction mixture and extraction is carried out 3 times with ethyl acetate. The combined organic phases are washed with saturated NaCl solution, dried over sodium sulfate, concentrated by rotary evaporation and purified by chromatography (silica gel: Merck 60; eluant: hexane/ethyl acetate 2:1 with 1% triethylamine). 568 mg of product are obtained (yield 86%, red oil).

EXAMPLE 16

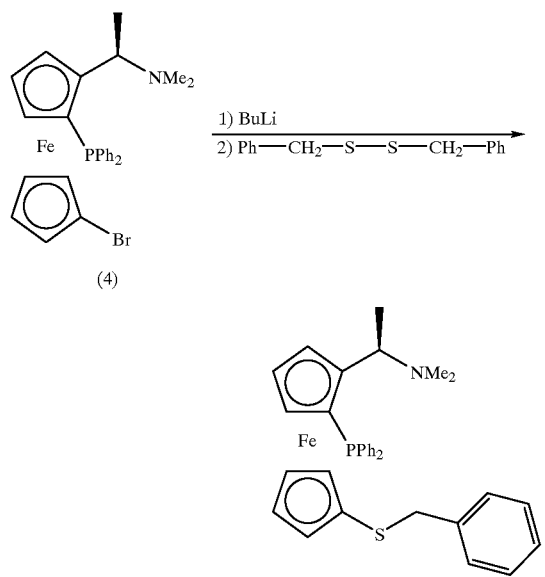

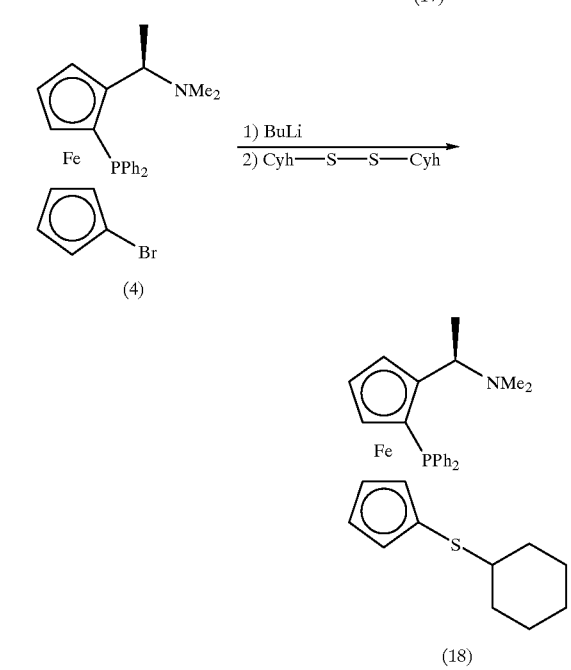

Compound (17)

(17) is prepared analogously to (11) starting from 0.48 mmol of (4) and 0.64 mmol of dibenzyl disulfide (duration of the reaction 12 hours). The crude product is extracted in water/ethyl acetate and purified by chromatography (eluant: ethyl acetate). Yield: 70% (orange, almost solid oil)

Compound (18)

(18) is prepared analogously to (17). Purification by chromatography (eluant: hexane/ethyl acetate 1:1) yields the product in a yield of 86% (orange, almost solid oil).

Characteristic NMR signals of compounds containing sulfur

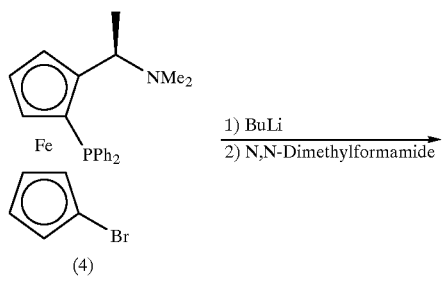

| Comp No. | R | R' | $^1$H-NMR (δ) | $^{31}$P-NMR (δ) |
|---|---|---|---|---|
| (10) | S—Ph | Br | 7.00–7.25(m, 5H, SPh) | — |
| (111) | S—Ph | PPh$_2$ | 6.95–7.20(m, 5H, SPh) 7.20–7.45(m, 10H, PPh$_2$) | −18.3 |
| (113) | S—Ph | P(Cyh)$_2$ | 0.9–1.4(m, PCyh$_2$) 6.95–7.20(m, 5H, SPh) | −8.66 |
| (112) | PPh$_2$ | S—Ph | 1.38(d, 3H, J=7, CH—CH$_3$) 6.95–7.55(m, 15H, SPh and PPh$_2$) | −24.4 |
| (17) | PPh$_2$ | S—CH$_2$—Ph | 3.66(s, 2H, CH$_2$—Ph) | −22.6 |
| (18) | PPh$_2$ | S—Cyh | 2.5(m, 1H, S—CH) | −22.4 |

EXAMPLE 17

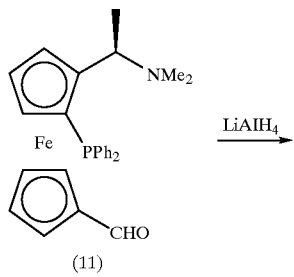

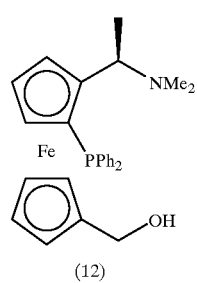

Compound (11)

1.3 Equivalents of a 1.6M solution of n-butyllithium in hexane are added dropwise at approximately −40° C. to a solution of 2.88 mmol of (4) in diethyl ether (10 ml per mmol of (4)), and the mixture is stirred at that temperature for a further 30 minutes. The reaction with 2.8 mmol of N,N-dimethylformamide is carried out at −78° C. The reaction mixture is then stirred at 25° C. for 4 hours, concentrated by rotary evaporation and extracted in toluene/water. The organic phase is dried with sodium sulfate and concentrated by rotary evaporation, and the crude product is purified by chromatography (silica gel Merck 60, eluant: hexane/ethyl acetate 1:1). Yield 84% (red, viscous oil).

Compound (12)

A mixture of 0.46 mmol of (11) in diethyl ether (10 ml per mmol of starting material) and 1.9 mmol of lithium aluminium hydride is stirred at room temperature for 2 hours. There are then added first 0.2 ml of water and, once the evolution of hydrogen has subsided, diethyl ether and sodium sulfate, the mixture is filtered, the solution is concentrated by rotary evaporation and the crude product is purified by chromatography (eluant: ethanol). Yield 80% (red viscous oil).

EXAMPLE 18

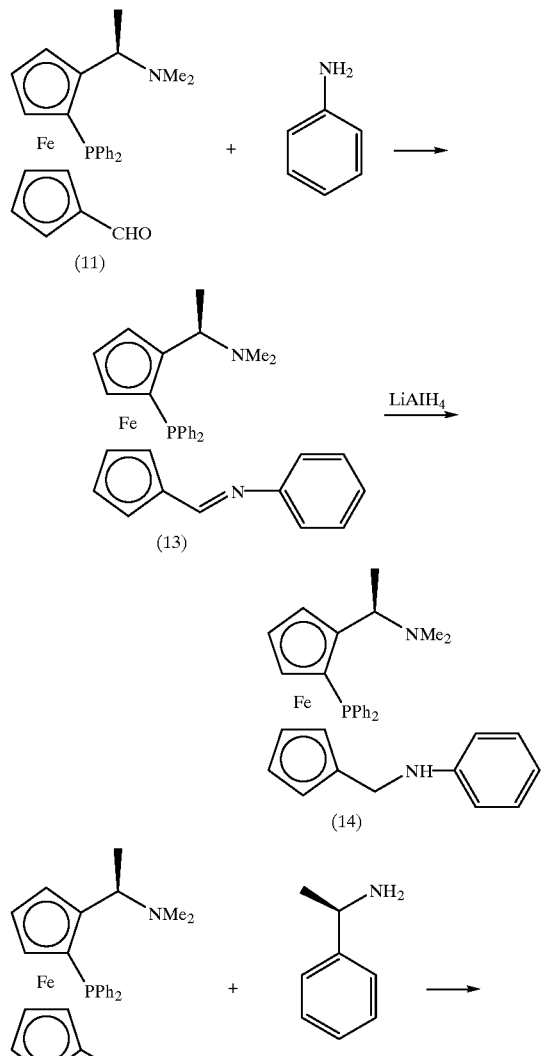

-continued

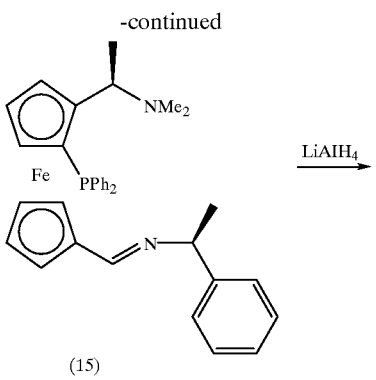

Compound (13)

A mixture of 0.53 mmol of (11), 0.56 mmol of aniline and 0.5 g of molecular sieves is stirred in 3 ml of toluene at room temperature for approximately 20 hours. The mixture is then filtered, the molecular sieves are washed with a small amount of methylene chloride and the solution is concentrated by rotary evaporation. A viscous red oil is obtained in quantitative yield.

Compound (14)

0.24 mmol of (13) is reduced with 1 mmol of lithium aluminium hydride as described for (12). Purification by chromatography (eluant: EtOH) yields the product in a 90% yield (yellow, solid).

Compounds (15) and (16)

(15) is prepared analogously to (13) with S-2-phenylethylamine and (16) is prepared analogously to (15). Yield (16): 89% (yellow, solid)

EXAMPLE 19

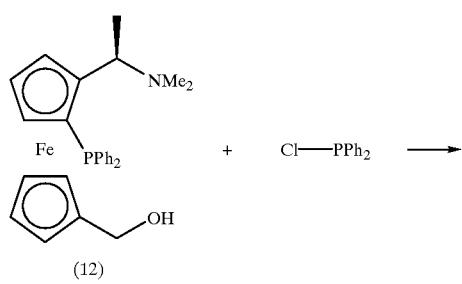

-continued

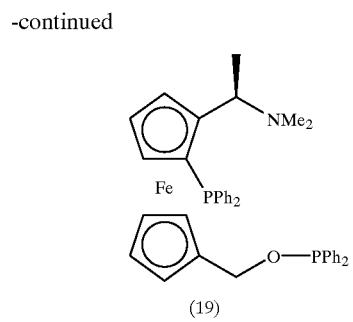

0.27 mmol of chloro-diphenylphosphine is added dropwise at 50° C. to 0.22 mmol of (12) and 0.34 mmol of triethylamine in 3 ml of toluene. After 2 hours' stirring, the mixture is allowed to cool and the resulting cloudy orange mixture is purified by chromatography (eluant: ethyl acetate/triethylamine 100:1). The product is obtained in a yield of 52% (yellow-orange, almost solid).

Characteristics NMR signals of compounds (11) to (16) and (19)

| Comp No. | R | $^1$H-NMR (δ) | $^{31}$P-NMR (δ) |
|---|---|---|---|
| (11) | CHO | 9.54(s, 1H, CHO) | −23.2 |
| (12) | CH$_2$OH | 3.96–4.08(d of d, 2H, CH$_2$OH) | −22.3 |
| (13) | CH=N—Ph | 7.92(s, 1H, CH=H) | −22.6 |
| (14) | CH$_2$—NH—Ph | 3.52–3.67(d of d, 2H, CH$_2$—NH) | −22.4 |
| (15) | CH=N—CH(CH$_3$)Ph | 1.50(d, 3H, N—CH(CH$_3$)Ph) 7.76(s, 1H, CH=N) | −22.5 |
| (16) | CH$_2$—NH—CH(CH$_3$)Ph | 1.26(d, 3H, N—CH(CH$_3$)Ph) 2.9–3.16(d of d, 2H, CH$_2$—NH) | −22.2 |
| (19) | CH$_2$—O—PPh$_2$ |  | −22.2 (cp-PPh$_2$) +113.7 (O—PPh$_2$) |

EXAMPLE 20

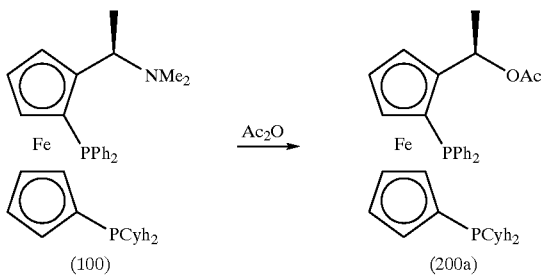

A solution of 206 mg (0.32 mmol) of (100) in 8 ml of acetic anhydride is stirred at room temperature for 24 hours. The orange solution is then extracted by shaking in aqueous NaCl solution and toluene, and the organic phase is washed with NaCl solution, dried over sodium sulfate and concentrated by rotary evaporation. 210 mg of crude product are obtained (orange almost solid oil), which is reacted further without purification.

$^1$H-NMR (CDCl$_3$) characteristic signals: δ 1.15 (s, C(O)CH$_3$), 6.19 (m, 1H, CH(CH$_3$)OAc.

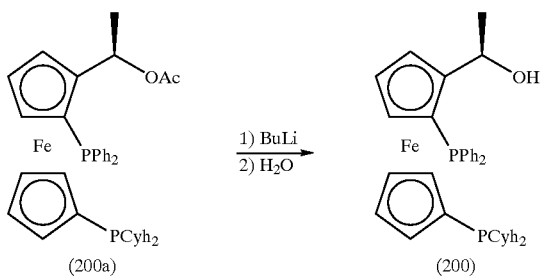

0.5 ml of a 1.6M BuLi solution in hexane is added dropwise with stirring at 0° C. to a mixture of 200 mg of the crude product (200a) i 10 ml of either, and the mixture is stirred further for 2.5 hours at 0° C. At 0° C., 20 ml of water are then added to the mixture and extraction is carried out with ether. The organic phase is dried with sodium sulfate, concentrated by rotary evaporation and purified by chromatography (silica gel: Merck 60; eluant: ethyl acetate/hexane 1/2). 55 mg of product are obtained (yield 27% based on (100), viscous orange oil).

Analysis $^1$H-NMR (CDCl$_3$) characteristic signals: δ 1.48 (d, 3H, C—CH$_3$), 3.7–4.5 (m, 7H, C$_5$H$_3$FeC$_5$H$_4$), 4.95 (m, 1H, CH—CH$_3$), 7.2–7.6 (m, 10H, P(C$_6$H$_5$)$_2$. $^{31}$P-NMR (CDCl$_3$): δ −7.1, −22.9

Application Examples

Hydrogenation of acetamidocinnamic acid methyl ester

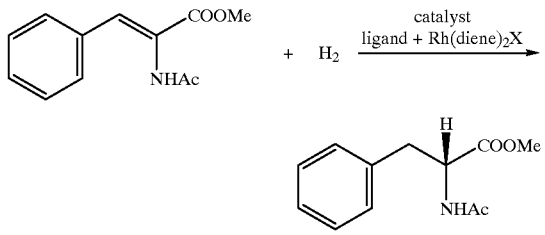

General: All the operations are carried out under inert gas. The hydrogenations are carried out in a 25 ml glass flask equipped with a magnetic stirrer (1500 rpm), an inert gas connection and a rubber septum. The reactants and the hydrogen are introduced using syringes and needles. All hydrogenations are carried out under normal hydrogen pressure.

Procedure: 0.018 mmol of ligand and 0.015 mmol of [Rh(diene)$_2$]X are dissolved in a 3 ml of MeOH in the hydrogenation vessel equipped with a magnetic stirrer and the solution is stirred for 10 minutes. To that catalyst precursor there is then added a solution of 1.5 mmol of acetamidocinnamic acid methyl ester in 7 ml of MeOH. Prior to each hydrogenation the inert gas in the hydrogenation vessel is displaced by hydrogen in 4 cycles (vacuum, normal hydrogen pressure). Hydrogenation is started by switching on the stirrer. The conversion is determined in each case by the consumption of hydrogen or by means of GC (column OV 101) and the optical yield is determined by means of GC (column: Chiracil-val). The results are given in the following Table:

TABLE 4

| Example No. | Ligand | Conf. of ligand | Rh(diene)$_2$X | Conversion [%] | Time [h] | ee | Conf. of product |
|---|---|---|---|---|---|---|---|
| 30 | (111) | S, R | Rh(COD)$_2$BF$_4$ | 83 | 6* | 44 | S |
| 31 | (113) | S, R | Rh(COD)$_2$BF$_4$ | 98 | 7* | 24 | S |
| 32 | (15) | S, R | RH(NBD)$_2$BF$_4$ | 90 | 21 | 16 | R |
| 33 | (103) | R, S | Rh(NBD)$_2$BF$_4$ | 83 | 16 | 83 | R |
| 34 | (103) | R, S | Rh(COD)$_2$BF$_4$ | 100 | 0.8* | 79 | R |
| 35 | (102) | S, R | Rh(COD)$_2$BF$_4$ | 100 | 5 | 76 | S |
| 36 | (13) | S, R | Rh(NBD)$_2$BF$_4$ | 95 | 24 | 52 | R |
| 37 | (14) | S, R | Rh(NBD)$_2$BF$_3$ | 66 | 19 | 71 | R |
| 38 | (16) | S, R | Rh(NBD)$_2$BF$_4$ | 77 | 25 | 67 | R |
| 39 | (17) | S, R | Rh(NBD)$_2$BF$_4$ | 88 | 18 | 49 | R |
| 40 | (18) | S, R | Rh(NBD)$_2$BF$_4$ | 95 | 22 | 62.5 | R |

*Addition of 10 microliters of MeSO$_3$H before the hydrogenation

Hydrogenation of keto-pantolactone

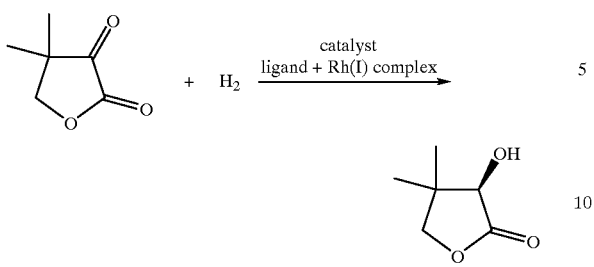

General: All the operations are carried out under inert gas. The hydrogenations are carried out in a 50 ml steel autoclave equipped with a magnetic stirrer (1500 rpm). The reactants and the hydrogen are introduced using syringes and needles. All hydrogenations are carried out at 50 bar hydrogen pressure.

Procedure: 0.0096 mmol of ligand and 0.008 mmol of Rh(I) complex are dissolved in 3 ml of solvent in a vessel equipped with a magnetic stirrer and the solution is stirred for 10 minutes. The solution is introduced into the autoclave against a current of argon. To that catalyst precursor there is then added a solution of 4 mmol of ketopantolactone in 5 ml of solvent. Prior to each hydrogenation the inert gas in the autoclave is displaced by hydrogen in 4 cycles (vacuum, normal hydrogen pressure). Hydrogenation is started by switching on the stirrer and terminated after 20 hours. The conversion and the optical yield are determined by means of GC (columns: OV 101, Lipodex-E). The results are given in the following Table 5:

What is claimed is:

1. A compound of formula

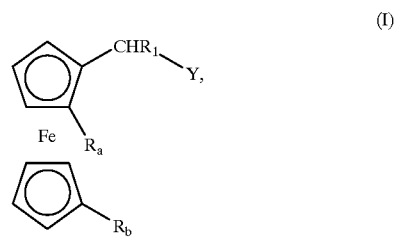

$R_1$ is $C_1$–$C_8$alkyl, $C_5$–$C_{12}$cycloalkyl, phenyl or phenyl substituted by from 1 to 3 substituents selected from $C_1$–$C_4$alkyl and $C_1$–$C_4$alkoxy;

$R_a$ is —$P(R_{10}R_{11})$ or —$SR_{12}$;

$R_b$ is —$P(R'_{10}R'_{11})$, —$SR'_{12}$, —CH=$NR_{12}$, —$CH_2$—NH—$R_{12}$ or —$CH_2$—O—$P(R_{10}R_{11})$;

$R_{10}$ and $R_{11}$ are each independently of the other $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —$SiR_4R_5R_6$, halogen, —$SO_3M$, —$CO_2M$, $PO_3M$, —$NR_7R_8$, —{$^+NR_7R_8R_9$}$X^-$ and $C_1$–$C_5$fluoroalkyl; or $R_{10}$ and $R_{11}$ together are $C_4$–$C_8$alkylene, $C_4$–$C_8$alkylene substituted by $C_1$–$C_4$alkyl or by phenyl, or annelated $C_4$–$C_8$alkylene;

$R'_{10}$ and $R'_{11}$ are each independently of the other as defined for $R_{10}$ and $R_{11}$, with the proviso that —$P(R_{10}R_{11})$ is not identical to —$P(R'_{10}R'_{11})$;

TABLE 5

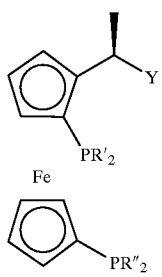

| Ex. No. | Ligand | R' | R" | Conf. | Rh(I) complex | T °C. | Solvent | Conversion | ee | Conf. |
|---|---|---|---|---|---|---|---|---|---|---|
| 41 | 100 | Ph | Cyh | R,S | [Rh(COD)Cl]$_2$ | 50 | THF | 98 | 77 | S |
| 42 | 101 | Ph | Cyp | R,S | [Rh(COD)Cl]$_2$ | 50 | THF | 100 | 65 | S |
| 43 | 109 | o-Tol | Cyh | S,R | [Rh(COD)Cl]$_2$ | 50 | THF | 100 | 72 | R |
| 44 | 109 | o-Tol | Cyh | S,R | [Rh(NBD)OAc]$_2$ | 50 | THF | 100 | 75 | R |
| 45 | 109 | o-Tol | Cyh | S,R | [Rh(NBD)OAc]$_2$ | 50 | Tol | 100 | 81 | R |
| 46 | 109 | o-Tol | Cyh | S,R | [Rh(NBD)OAc]$_2$ | 25 | Tol | 100 | 84 | R |
| 47 | 105 | p-PhCF$_3$ | Cyh | R,S | [Rh(COD)Cl]$_2$ | 50 | THF | 95 | 67 | S |
| 48 | 200 | Ph | Cyh | R,S | [Rh(COD)Cl]$_2$ | 50 | THF | 100 | 65 | S |

Y is NMe$_2$ in Ex. No. 41 to 47 and Y is OH in Ex. No. 48

$R_{12}$ is H, $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$ cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —{$^+NR_7R_8R_9$}$X^-$ and $C_1$–$C_5$fluoroalkyl;

R'$_{12}$ is as defined for R$_{12}$, with the proviso that —SR$_{12}$ is not identical to —SR'$_{12}$;

R$_4$, R$_5$ and R$_6$ are each independently of the others C$_1$–C$_{12}$alkyl or phenyl;

R$_7$ and R$_8$ are each independently of the other H, C$_1$–C$_{12}$alkyl or phenyl, or R$_7$ and R$_8$ are tetramethylene, pentamethylene or 3-oxa-1,5-pentylene, R$_9$ is H or C$_1$–C$_4$alkyl;

M is H or an alkali metal;

X$^-$ is the anion of an acid;

Y is —OR$_{13}$, —SR$_{14}$ or —NR$_{15}$R$_{16}$;

R$_{13}$ is H, C$_1$–C$_{18}$alkyl, —C(O)—C$_{1-8}$alkyl, phenyl or phenyl substituted by from one to three substituents selected from C$_1$–C$_4$alkyl, C$_1$–C$_4$alkoxy, —SiR$_4$R$_5$R$_6$, halogen, —SO$_3$M, —CO$_2$M, —PO$_3$M, —NR$_7$R$_8$, —{$^+$NR$_7$R$_8$R$_9$}X$^-$ and C$_1$–C$_5$fluoroalkyl;

R$_{14}$ is H, C$_1$–C$_{18}$alkyl, phenyl or phenyl substituted by from one to three substituents selected from C$_1$–C$_4$alkyl, C$_1$–C$_4$-alkoxy, —SiR$_4$R$_5$R$_6$, halogen, —SO$_3$M, —CO$_2$M, —PO$_3$M, —NR$_7$R$_8$, {$^+$NR$_7$R$_8$R$_9$}X$^-$ and C$_1$–C$_5$-fluoroalkyl; and R$_{15}$ and R$_{16}$ are each independently of the other C$_1$–C$_{18}$alkyl that may be substituted and/or interrupted by one or more hetero atoms, arylenes or carbocycles; or —NR$_{15}$R$_{16}$ is a cyclic amine with the proviso that formula (I) does not embrace a compound in which R$_1$ is —CH$_3$ and Y is —N(CH$_3$)$_2$, when R$_a$ is —P(C$_6$H$_5$)$_2$ and R$_b$ is —P{C(CH$_3$)$_3$}$_2$ or when R$_a$ is —P{C(CH$_3$)$_3$}$_2$ and R$_b$ is —P(C$_6$H$_5$)$_2$.

2. A compound of formula (I) according to claim 1 that corresponds to one of the formulae (Ia), (Ib), (Ic) and (Id)

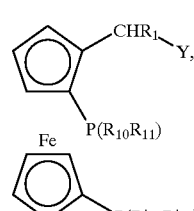

(Ia)

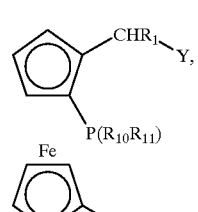

(Ib)

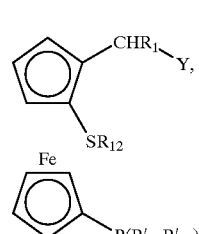

(Ic)

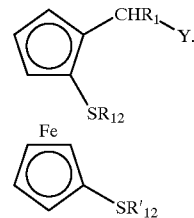

(Id)

3. A compound of formula (I) according to claim 1, wherein

R$_{10}$ and R$_{11}$ are each independently of the other C$_1$–C$_{12}$alkyl, C$_1$–C$_{12}$alkyl substituted by C$_1$–C$_4$alkoxy, C$_5$–C$_{12}$cycloalkyl or by phenyl, C$_5$–C$_{12}$cycloalkyl, phenyl, C$_5$–C$_{12}$cycloalkyl substituted by C$_1$–C$_4$alkyl or by C$_1$–C$_4$alkoxy, or phenyl substituted by from one to three substituents selected from C$_1$–C$_4$alkyl, C$_1$–C$_4$alkoxy, —SiR$_4$R$_5$R$_6$, halogen, —SO$_3$M, —CO$_2$M, —PO$_3$M, —NR$_7$R$_8$, {$^+$NR$_7$R$_8$R$_9$}X$^-$ and C$_1$–C$_5$fluoroalkyl; or the group —P(R$_{10}$R$_{11}$) is a radical of formula IV, IVa, IVb or IVc

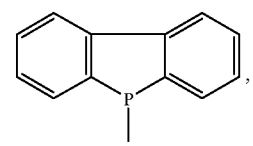

(IV)

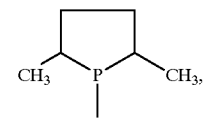

(IVa)

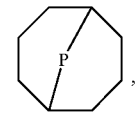

(IVb)

(IVc)

4. A compound of formula (I) according to claim 1, wherein R$_{10}$, R'$_{10}$, R$_{11}$, R'$_{11}$, R$_{12}$ and R'$_{12}$ are each independently of the others cycloalkyl having from 5 to 8 carbon atoms.

5. A compound of formula (I) according to claim 1, wherein R$_{10}$, R'$_{10}$, R$_{11}$, R'$_{11}$, R$_{12}$ and R'$_{12}$ are each independently of the others unsubstituted phenyl or phenyl substituted by 1 or 2 substituents.

6. A compound of formula (I) according to claim 1, wherein R$_{10}$, R'$_{10}$, R$_{11}$, R'$_{11}$, R$_{12}$ and R'$_{12}$ are each independently of the others 2-methyl-, 3-methyl-, 4-methyl-, 2- or 4-ethyl, 2- or 4-isopropyl-, 2- or 4-tert-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-SO₃H-, 2- or 4-SO₃Na-, 2- or 4-{⁺NH₃Cl⁻}-, 3,4,5-trimethyl-, 2,4,6-trimethyl-, 4-trifluoromethyl- or 3,5-di(trifluoromethyl)-phen-1-yl.

7. A compound of formula (I) according to claim 1, wherein $R_{10}$, $R'_{10}$, $R_{11}$, $R'_{11}$, $R_{12}$, $R'_{12}$, are each independently of the others cyclohexyl, n-butyl, isobutyl, tert-butyl, phenyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl.

8. A compound of formula (I) according to claim 1, wherein Y is —$OR_{13}$ or —$NR_{15}R_{16}$.

9. A compound of formula (I) according to claim 1, wherein Y is —$OR_{13}$ or —$NR_{15}R_{16}$ in which $R_{13}$ is H, $C_1$–$C_4$alkyl or phenyl and $R_{15}$ and $R_{16}$ are each independently of the other $C_1$–$C_{18}$-alkyl.

10. A compound of formula (VIb)

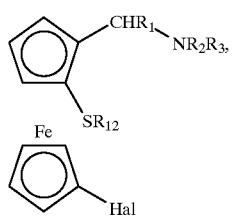

(VIb)

$R_1$ is $C_1$–$C_8$alkyl, $C_5$–$C_{12}$cycloalkyl, phenyl or phenyl substituted by from 1 to 3 substituents selected from $C_1$–$C_4$alkyl and $C_1$–$C_4$alkoxy;

$R_2$ and $R_3$ are each independently of the other hydrogen or $C_1$–$C_{12}$alkyl;

$R_{12}$ is H, $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —{N⁺$R_7R_8R_9$}X⁻ and $C_1$–$C_5$fluoroalkyl;

$R_4$, $R_5$ and $R_6$ are each independently of the other $C_1$–$C_{12}$alkyl or phenyl;

$R_7$ and $R_8$ are each independently of the other H, $C_1$–$C_{12}$alkyl or phenyl, or $R_7$ and $R_8$ together are tetramethylene, pentamethylene or 3-oxa-1,5-pentylene, $R_9$ is H or $C_1$–$C_4$alkyl;

M is H or an alkali metal;

X⁻ is the anion of an acid; and

Hal is F, Cl, Br or I.

11. A process for the preparation of a compound of formula (Ia), (Ib), (Ic) or (Id) according to claim 2, in which process (a) in an inert organic solvent, alkyllithium is added to a compound of formula

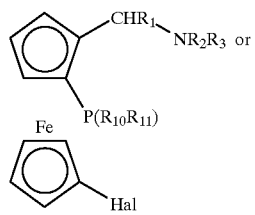

(VIa)

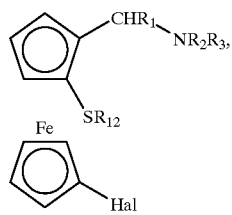

(VIb)

$R_1$ is $C_1$–$C_8$alkyl, $C_5$–$C_{12}$cycloalkyl, phenyl or phenyl substituted by from 1 to 3 substituents selected from $C_1$–$C_4$alkyl and $C_1$–$C_4$alkoxy;

$R_2$ and $R_3$ are each independent of the other hydrogen or $C_1$–$C_{12}$alkyl;

Hal is F, Cl, Br or I;

$R_{10}$ and $R_{11}$ are each independently of the other $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —{⁺$^{NR}R_8R_9$}X⁻ and $C_1$–$C_5$fluoroalkyl; or $R_{10}$ and $R_{11}$ together are $C_4$–$C_8$alkylene, $C_4$–$C_8$alkylene substituted by $C_1$–$C_4$alkyl or by phenyl, or annelated $C_4$–$C_8$ alkylene;

$R_{12}$ is H, $C_1$–$C_{12}$alkyl, $C_1$–$C_{12}$alkyl substituted by $C_1$–$C_4$alkoxy, $C_5$–$C_{12}$cycloalkyl or by phenyl, $C_5$–$C_{12}$cycloalkyl, phenyl, $C_5$–$C_{12}$cycloalkyl substituted by $C_1$–$C_4$alkyl or by $C_1$–$C_4$alkoxy, or phenyl substituted by from one to three substituents selected from $C_1$–$C_4$alkyl, $C_1$–$C_4$alkoxy, —$SiR_4R_5R_6$, halogen, —$SO_3M$, —$CO_2M$, —$PO_3M$, —$NR_7R_8$, —{⁺$NR_7R_8R_9$}X⁻ and $C_1$–$C_5$fluoroalkyl;

$R_4$, $R_5$ and $R_6$ are each independently of the others $C_1$–$C_{12}$alkyl or phenyl;

$R_7$ and $R_8$ are each independently of the other H, $C_1$–$C_{12}$alkyl or phenyl, or $R_7$ and $R_8$ together are tetramethylene, pentamethylene or 3-oxa-1,5-pentylene, $R_9$ is H or $C_1$–$C_4$alkyl;

M is H or an alkali metal;

X⁻ is the anion of an acid;

and the mixture is caused to react; and (b) either a compound of formula (VIa) or a compound of formula (VIb) is reacted with a compound of formula $R'_{12}SSR'_{12}$ (Vc) or ClP($R'_{10}R'_{11}$) (Vd) in which $R'_{10}$ and $R'_{11}$ are each independently of the other as defined for $R_{10}$ and $R_{11}$, with the proviso that —P($R_{10}R_{11}$) is not identical to —P($R'_{10}R'_{11}$) and $R'_{12}$ is as defined for $R_{12}$ with the proviso that $R_{12}$ is not identical to $R'_{12}$, and optionally the radical —$NR_2R_3$ is converted into the radical —Y, wherein Y is —OR$_{13}$, —SR$_{14}$ or —NR$_{15}$R$_{16}$;

R$_{13}$ is H, C$_1$–C$_{18}$alkyl, —C(O)—C$_{1-8}$alkyl, phenyl or phenyl substituted by from one to three substituents selected from C$_1$–C$_4$alkyl, C$_1$–C$_4$alkoxy, —SiR$_4$R$_5$R$_6$, halogen, —SO$_3$M, —CO$_3$M, —CO$_2$M, —PO$_3$M, —NR$_7$R$_8$, —{$^+$NR$_7$R$_8$R$_9$}X$^-$ and C$_1$–C$_5$fluoroalkyl;

R$_{14}$ is H, C$_1$–C$_{18}$alkyl, phenyl or phenyl substituted by from one to three substituents selected from C$_1$–C$_4$alkyl, C$_1$–C$_4$-alkoxy, —SiR$_4$R$_5$R$_6$, halogen, —SO$_3$M, —CO$_2$M, —PO$_3$M, —NR$_7$R$_8$, —{$^+$NR$_7$R$_8$R$_9$}X$^-$ and C$_1$–C$_5$-fluoroalkyl; and R$_{15}$ and R$_{16}$ are each independently of other other C$_1$–C$_{18}$alkyl that may be substituted and/or interrupted by one or more hetero atoms, arylenes or carbocycles; or —NR$_{15}$R$_{16}$ is a cyclic amine.

12. A transition metal complex containing as a ligand a compound of formula (I) according to claim 1.

13. A transition metal complex according to claim 12, wherein the transition metal is Rh, Ir, Ru, Pd, Ni or Au.

14. A process for the enantioselective catalysis of reactants, wherein the process comprises contacting the reactants with a transition metal complex containing as a ligand a compound of formula (I) as claimed in claim 1.

15. The process according to claim 14 wherein the transition metal is thodium or iridium, and a reactant contains a carbon/carbon or carbon/hetero atom double bond that is hydrogenated.

* * * * *